United States Patent [19]
Dezael et al.

[11] Patent Number: 6,114,178
[45] Date of Patent: Sep. 5, 2000

[54] DEVICE FOR REMOVING AND/OR INJECTING A FLUID SAMPLE ENABLING THE CHEMICAL AND/OR THERMODYNAMIC EQUILIBRIUM TO BE PRESERVED

[75] Inventors: Claude Dezael, Maisons Lafitte; Fabrice Lecomte, Rueil Malmaison, both of France

[73] Assignee: Institut Francais du Petrole, Cedex, France

[21] Appl. No.: 09/104,383

[22] Filed: Jun. 25, 1998

[30] Foreign Application Priority Data

Jun. 25, 1997 [FR] France .................................. 97 08080

[51] Int. Cl.$^7$ ...................................................... G01N 1/14
[52] U.S. Cl. ........................... 436/180; 436/174; 422/81; 422/100; 73/863.11; 73/864.1
[58] Field of Search .................................. 422/63, 67, 81, 422/100, 105, 109; 436/54, 174, 180; 73/863.11, 863.81, 863.84, 864.01

[56] References Cited

U.S. PATENT DOCUMENTS

| | | | |
|---|---|---|---|
| 4,269,608 | 5/1981 | Sisti et al. ..................................... | 55/67 |
| 4,289,029 | 9/1981 | Sampson et al. ..................... | 73/863.11 |
| 4,357,136 | 11/1982 | Herskovitz et al. ..................... | 433/224 |
| 4,484,061 | 11/1984 | Zelinka et al. ........................... | 219/301 |
| 4,684,344 | 8/1987 | Brockway ................................... | 433/81 |
| 4,695,125 | 9/1987 | Sinclair et al. ......................... | 350/96.2 |
| 5,088,335 | 2/1992 | LaFreniere et al. .................... | 73/864.6 |
| 5,152,678 | 10/1992 | Zeck ......................................... | 417/401 |
| 5,275,786 | 1/1994 | Soleta et al. .............................. | 422/81 |
| 5,738,658 | 4/1998 | Maus et al. .............................. | 604/151 |
| 5,817,954 | 10/1998 | Kahng et al. ......................... | 73/863.84 |
| 5,918,258 | 6/1999 | Bowers ................................... | 73/24.06 |

FOREIGN PATENT DOCUMENTS

| | | |
|---|---|---|
| 0367899 | 5/1990 | European Pat. Off. . |
| 0455333 | 11/1991 | European Pat. Off. . |
| 9502764 | 1/1995 | WIPO . |

*Primary Examiner*—Long V. Le
*Attorney, Agent, or Firm*—Antonelli, Terry, Stout & Kraus, LLP

[57] ABSTRACT

The invention is a process for analyzing a fluid sample. The process includes collecting a fluid sample in a sampling unit having a cavity for containing the fluid, at least one passage used which connects the cavity to a source of the fluid sample to aspirate the fluid sample from the fluid sample source into the cavity and from which the fluid sample is injected into an analyzer device, a pressure varying device disposed in the cavity which provides control of pressure of the fluid sample in the cavity and a heat source which heats the fluid sample in the cavity; controlling at least one of the pressure of the fluid sample in the cavity with the pressure varying device and the temperature of the fluid sample in the cavity with the heat source to maintain the sample in the cavity to have at least one of pressure and temperature substantially identical to at least one of the pressure and temperature of the sample at a time of collection in the cavity from the fluid source; and injecting the fluid sample from cavity into the analyzer device with at least one of the temperature and the pressure substantially identical to at least one of the temperature and the pressure of the fluid sample in the cavity at the time of collection and thereafter analyzing the fluid sample.

21 Claims, 1 Drawing Sheet

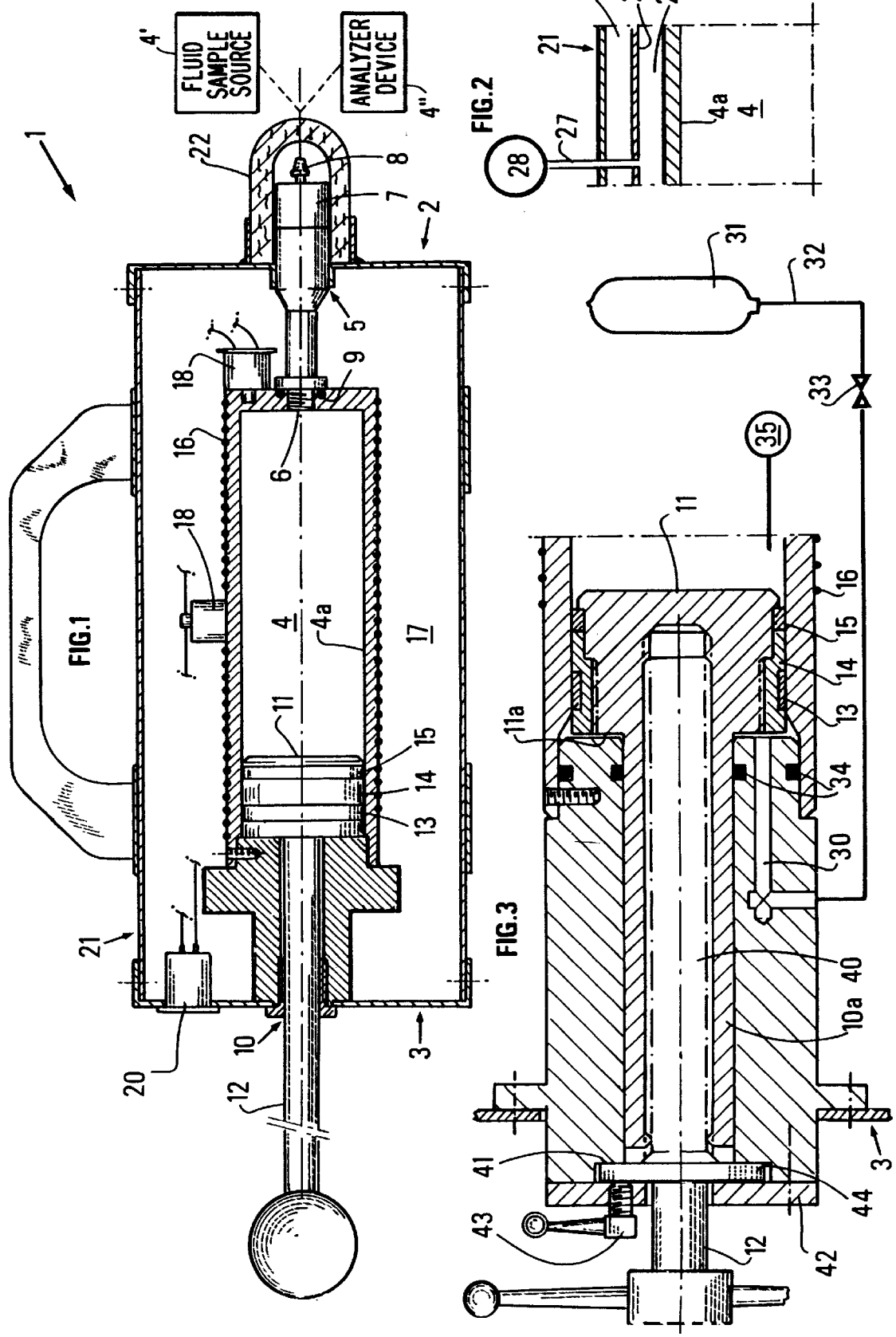

DEVICE FOR REMOVING AND/OR INJECTING A FLUID SAMPLE ENABLING THE CHEMICAL AND/OR THERMODYNAMIC EQUILIBRIUM TO BE PRESERVED

BACKGROUND OF THE INVENTION

1. Field of the Invention

The present invention relates to a device for removing and/or injecting a fluid such as a gas, a liquid, or a gas-liquid mixture which is in a given state, without disturbing this state.

The word "state" is intended to signify for example a state of equilibrium in which a fluid.

2. Description of the Prior Art

When a fluid, for example a noncondensable gas or liquid with a low viscosity, is analyzed in a temperature range between 0 and 40° C., the sample removal stage does not introduce any marked change into the composition of these fluids. Generally such sampling is done by drawing samples up into a pipes of the sampling units by means of a syringe. The fluids to be analyzed can be mixtures of gases such as oxygen, nitrogen, carbon dioxide, carbon monoxide, methane, ethane, or liquids whose boiling points are greater than room temperature and liquids with low viscosity, less than 20 centistokes for example.

When the fluids include products or components that can react with each other when an external parameter varies, for example a thermodynamic parameter, the chemical and/or thermodynamic equilibrium may shift irreversibly, modifying the nature of the fluid and leading to a non-representative analysis of the fluid.

This change in nature may be encountered in mixtures containing condensable products such as $H_2O$, $SO_2$, pentane, or butane in specific temperature ranges, heavy hydrocarbons in the presence of noncondensable products, or more generally products whose compositions at equilibrium may change with temperature or pressure, such as azeotropes.

This is the case for example of a gas containing hydrogen sulfide and sulfur dioxide $SO_2$ that react in the balanced reaction $2\ H_2S+SO_2 \rightarrow 3\ S+2\ H_2O$. A drop in temperature shifts the reaction rightward leading to production of liquid or solid sulfur and water. The analysis of this gas is not representative because sulfur and water are added in the analysis to the initial components $H_2S$ and $SO_2$.

This is also the case when analyzing combustion fumes containing sulfur dioxide and large quantities of water. A drop in temperature below the dewpoint inevitably causes the content of the gas, $SO_2$, and $SO_3$ sampled to drop, causing an error in quantifying the components of these fumes, possibly a large error.

For liquids at risk of crystallizing or demixing (separation of liquid into several phases) when the temperature varies or liquids with high viscosities, the change in composition upon sampling may bring about substantial analysis errors.

It is thus desirable to have a device that will enable a fluid sample to be removed under conditions that will prevent any conversion of the fluid and store the fluid in a state substantially identical to the original state.

The prior art describes various types of devices for injecting and/or sampling products.

U.S. Pat. No. 4,684,344 describes a syringe comprising a heating means with a point action, namely concentrated more particularly in one spot. Contrary to the principle employed in the present invention, the teaching of this document is to cause a change in state of a product to bring it into a form in which it can be injected.

Due to industrial constraints demanding increasingly fine and precise analyses, it is desirable to have a device that will sample and/or inject a fluid whose state is likely to evolve due to for example a change in at least one thermodynamic parameter, while keeping this fluid in a given state.

The state of the fluid to be stored may correspond to a state of equilibrium which is the original state of the fluid in a processing unit.

SUMMARY OF THE INVENTION

A device according to the present invention keeps the fluid in a given state from the source location to an arrival location which can be the analysis locations avoiding an irreversible shift in the chemical equilibrium in the fluid, namely leading to a permanent change in its nature and/or its composition.

The word "state" is intended to signify for example of state of equilibrium in which a fluid may be.

The invention is applied in particular to the field of analyzing gases, liquefied gases, or liquids that have high vapor pressures of viscosities.

The invention avoids any change within the fluid during the operation in which the sample is injected into the analysis device.

The present invention relates to a sampling device for removing and/or injecting a fluid sample that is in an initial state, comprising a body with two ends, one of the ends being provided with at least one orifice allowing passage of the fluid, a cavity to receive the fluid sample, and means for aspirating and/or injecting the fluid sample. The invention maintains the sample in a state of chemical and/or thermodynamic equilibrium that is substantially identical to the original conditions of the fluid before removal and/or before injection.

The initial state may be determined by the chemical and/or thermodynamic equilibrium of the fluid before it was collected from a source location.

According to one embodiment, the device raises the temperature and/or regulates the temperature and/or raises the pressure and/or regulates the pressure.

According to one embodiment, a temperature-control allows the temperature to be held between 20° C. and 200° C., preferably between 20° C. and 150° C., a pressure-control maintains a pressure ranging between atmospheric pressure and 5 MPa, preferably between atmospheric pressure and 3 MPa.

A connecting device may include an automatic shutoff which are for example is controlled by the connection of the sampling device at the sampling point or at the analysis device.

The device can be connected to an outside energy source.

According to one embodiment of the invention, the outside device comprises an independent battery.

The device according to the invention is used in particular in different types of applications, particularly the following:

to remove a gas sample from a gas stream of a sulfur manufacturing unit,
 to remove a sample of combustion fumes containing the following compounds: $SO_2$, $SO_3$, $N_2$, $O_2$, $H_2O$, and $NO_x$, $H_2S$, $COS$, $CS_2$, $NH_3$, to remove a sample of a liquid likely to separate into several phases when the temperature or pressure changes, to remove a sample of gas containing components that are condensable at low temperature (e.g. butane or propane) in natural gas processing units.

BRIEF DESCRIPTION OF THE DRAWINGS

Other advantages and characteristics of the present invention will emerge from reading the description provided hereinbelow as embodiments in the framework of nonlimiting applications with reference to the attached drawings wherein:

FIG. 1 describes an example of the device according to the invention,

FIG. 2 shows schematically an alternative embodiment of the device in FIG. 1; and FIG. 3 shows in detail part of the device in FIG. 1 equipped with hydraulic or mechanical device for modifying the pressure in the cavity.

DESCRIPTION OF THE PREFERRED EMBODIMENTS

FIG. 1 describes a device which maintains a fluid in a given state, namely in a given chemical and/or thermodynamic equilibrium, for at least the duration of the sampling operation and until it is injected into an analysis device (not shown in this figure).

The device is for example in the form of a syringe with a body 1 having two ends 2, 3 and a cavity 4 which is connectable to a fluid source 4' and an analysis device 4".

One of the ends 2 is provided with at least one opening 5 which is fitted with removal and/or a injection means comprising a feed tip connected to a connecting tip 7, which is connected to a connector 8. This assembly is joined to cavity 4 by O-rings 9, thus providing a seal.

The syringe can also be equipped with a known automatic shutoff not shown in the figure. A check valve can be used to allow the fluid to pass only when the syringe is connected to the removal point. A slide valve, which can be controlled electrically, can also be used, actuation of which is controlled by the connection of the syringe to a sampling point in the unit from which the fluid sample is removed or in the analysis device into which the fluid sample is injected.

The other end 3 of the syringe may have at least one opening 10, or passage, in which a means for removing and/or injecting a fluid sample is disposed. This means is for example a plunger 11 connected to a control or displacement means 12. Plunger 11 moves for example by sliding inside cavity 4, being guided by a guide segment 13 integral with the inside wall 4a of cavity 4, the guide segment being supported by a segment holder 14. A seal 15 provides the seal between cavity 4 of the syringe and the outside when the plunger moves.

The syringe maintains the sample of fluid removed and/or injected in a substantially stable state of equilibrium during the removal and/or injection operations by maintaining the temperature of the cavity containing the fluid sample to be analyzed.

A heating resistor 16 is for example disposed around cavity 4 and over the majority of its length "l." Advantageously, this heating resistor may be accompanied by or associated with insulation 17 made of for example an insulating material surrounding the cavity and the heating resistor, thus ensuring that the syringe temperature is kept constant. In all cases, a thermal insulator means 17 ensures effective temperature maintenance that is stable in the course of time chosen to perform the removal and/or injection operations without any or with minimal temperature variation.

The heating resistor may be connected to an external energy source (battery) by means of a socket 20 built into the syringe.

Another possibility is to build an independent battery, not shown in the figure, into the syringe to deliver the necessary energy to heating resistor 16.

In this way, the state of the fluid sample in the sampling source, which may correspond to an equilibrium state of the components of the sampled fluid, is preserved sufficiently to prevent any change in the composition of this fluid.

Advantageously, this procedure enables the operations to be conducted with no introduction of additional energy, so that the syringe can be used in any environment.

The syringe can also be fitted with one or more temperature controls 18 such as a thermostat.

The temperatures can be monitored by a temperature-measuring and display probe of the mechanical or electrical type and, by means of a temperature-regulator means which is mechanical, electromechanical, or electronic, placed in a housing outside the syringe, not shown in the figure. The housing can also supply additional energy needed for heating the assembly, the additional energy being electrical energy for example.

The energy source can be a connection to line voltage and/or to a battery and/or a cell or a device for connecting to the line voltage and/or a battery or a cell. Thus it is possible to use means such as the cigarette lighter of an automobile or any other energy source in this vehicle.

According to another embodiment, the means for increasing and holding the temperature is a heat-carrying fluid, described in detail in FIG. 2.

The temperature values at which the syringe operates are between 20 and 200° C., preferably between 20 and 150° C.

Advantageously, insulation 22 may be disposed around the connection (tip and pipe) to prevent any temperature change that might occur when the syringe filled with the fluid sample is handled, for example between the removal point and the analysis device. The changes in temperature may appear if the unprotected tip is exposed to ambient temperature.

The insulation 17 and 22 is for example selected from the following list: glass wool, quartz wool, polystyrene, polyethylene, or any other material known to the individual skilled in the art. It is also possible to provide the device with a vacuum flask with double glass walls of the Dewar flask type to obtain a low heat loss, for example 10° C. per hour, for an internal temperature of 150° C. and an external temperature of 20° C. This low heat loss advantageously allows the syringe to be used under the sampling temperature conditions without it being necessary to provide additional external heat. This advantageously enables this device to be used in sensitive or hazardous utilization areas or in areas where explosion-proof materials are used. Upon the return to an explosion-proofed area, the heating and temperature maintenance may be accomplished by suitable electrical sources.

Cavity 4 can be in different geometric shapes and its volume can be chosen according to the fluid to be sampled. It varies for example from 0.1 $cm^3$ to 1 $dm^3$, preferably from 1 $cm^3$ to 500 $cm^3$.

The materials of which the syringe is composed, particularly the parts likely to be in contact with the fluid, for example inside wall 4a of cavity 4 and the feed tip are preferably inert to the fluids. The materials preferably chosen will thus be nickel, aluminum, titanium, and/or one of their alloys such as stainless steels, suitable plastics for example Teflon, kefel, or propylene, glass, quartz, or zirconium.

The coating of the inside walls of the syringe and the face of the plunger can also be a stainless steel coated with a chromium-oxide-based ceramic. Such a coating can also be provided on titanium. This improves the ability of the plunger to slide against the jacket.

FIG. 2 shows schematically in detail one embodiment in which the syringe is heated and kept hot by a heat-carrying fluid.

An envelope 25 impermeable to the fluid is disposed for example around cavity 4 in order to form a space 26 with its inside wall 4a. A pipe 27 provides the connection between space 26 and an external source 28 containing a heat-carrying fluid, designed to fill space 26.

This arrangement is of course provided at least at the two sides of cavity 4 and totally surrounds the holding cavity to prevent any heat loss.

In certain cases, it may be useful to combine the temperature-holding control with other devices for varying the pressure in cavity 4, with the actions of these two types of devices being either independent or complementary.

FIG. 3 shows schematically two examples of devices enabling the pressure in the cavity to be varied so as to re-establish the fluid equilibrium when the fluid is displaced by a minimal quantity, thus preventing any change in the composition of the fluid sample.

The pressure range in which the device operates is preferably from atmospheric pressure to 5 MPa and preferably from atmospheric pressure to 3 MPa.

According to a first embodiment, pressure control is of the hydraulic type. One of the ends of the syringe has at least one passage 30 that can be connected, with the aid of a pipe 32, to an external source 31 containing a fluid under pressure such as a compressed gas. Passage 30 communicates with cavity 4 of the syringe and emerges for example at face 11a of plunger 11. A sealing 34 is disposed at opening 10 to prevent the compressed gas filling the space formed by face 11a of the plunger and the end of the inside wall of the cavity from leaking when the plunger moves. A pressure gauge 35 connected to the cavity measures the fluid pressure in the cavity.

The plunger is thus moved by a quantity of compressed gas introduced through passage 30 which applies a sufficient force to face 11a of the plunger. The quantity of gas to be injected is regulated with the aid of a valve 33 for example on pipe 32 and controlled as a function of pressure gauge 35.

Another embodiment uses threaded rods to move the plunger.

One or more threaded rods are disposed at opening 10. This opening 10 can have a cylindrical shape and guide translationally a rod 10a translationally integral with plunger 11. In FIG. 3, rod 10a has an internal thread that cooperates with a threaded rod 40. This threaded rod 40 is immobilized translationally by a stop 41 while being free to rotate. The rotational movement of rod 40, provided by a displacement devices 12, for example, has the effect of displacing plunger 11 translationally by means of rod 10a.

Stop 41 is held relative to the syringe by a shoulder 44 and a cover 42. A lock 43 keeps the plunger in a given position.

The plunger is moved until the counterpressure necessary and sufficient to keep the fluid in and/or restore the sample to its initial state is obtained.

When the fluids removed are at higher than atmospheric pressure, rod 10a can simply press against face 11b of plunger 11 to obtain the desired counterpressure effect.

The syringe can also have a knob by which it can be easily moved.

The syringe can be used to carry out various sampling operations, some of which are described hereinbelow indicatively and not limitatively.

EXAMPLE 1

When a gas sample is to be taken from a gas stream in a sulfur manufacturing unit to analyze it, a syringe such as that described in FIG. 1 is used, with the following characteristics:

a capacity of approximately 200 $cm^3$, the parts of the syringe in contact with the gas to be sampled are made of glass for example for the inside walls of the syringe and the plunger, kelef for the seals, and gold-coated stainless steel for the sampling tip.

The connection between the syringe and the gas stream is provided by a sampling tube preferably made of Teflon.

Removal is done at a removal temperature of between 140 and 150° C. so that the sulfur-containing compounds do not react with each other.

To set the syringe to the desired temperature, the syringe is heated in the laboratory for example to a temperature of substantially approximately 150° C. The temperature of the syringe is maintained by the insulating material. When this insulation is insufficient, the syringe can be connected to an independent battery and correct temperature maintenance can be monitored.

It is also possible to keep the syringe at the desired temperature by plugging it into the cigarette lighter of the vehicle in which the syringe is carried from the place where the desired thermodynamic conditions are established to its destination.

The internal temperature of the cavity that will receive the removed sample is kept at a temperature of substantially approximately 150° C., the syringe is connected to the gas stream, and the gas is sampled.

The time taken by the sampling operation until the vehicle returns or up to a point that the device can be connected to an external power source is approximately 30 minutes and the temperature change from the original temperature is $-5°$ C. The original temperature is reached after approximately 5 minutes. This temperature is held and regulated by plugging the syringe into the cigarette lighter up to the analysis location and the gas sample can be analyzed with a chromatograph for example at a temperature that is approximately the same as the temperature in the unit.

EXAMPLE 2

The syringe according to the invention is advantageously used to remove a sample of combustion fumes containing the following compounds: $SO_2$, $SO_3$, $N_2$, $O_2$, $H_2O$, $NO_x$.

The specific characteristics of the syringe for conducting such an analysis are:

syringe body, plunger, tip, and removal tube made of stainless steel, seals of rubber such as viton.

When such samples are taken, the water content of the fumes is such that the drop in temperature causes the water to condense so that the $SO_2$, $SO_3$, and $NO_x$, content also decreases as these substances are dissolved in the condensed water, leading to errors when the gas sample is analyzed.

To avoid this loss of sought-after compounds, it is preferable to sample at a temperature higher than the condensation point of the water.

The syringe is first brought to a temperature of approximately 120° C., for example by a method substantially identical to the method described above. In this case, as the unit is not explosion-proof, it is possible to maintain the connection between the syringe and the portable battery so that the temperature is kept at the original temperature with no heat loss being recorded.

With this method, the sample removed undergoes no temperature change so that the analysis conducted, for example by luminescence chemistry, is representative of the combustion fumes.

EXAMPLE 3

The syringe described in FIG. 1 is used for example to make an analytical analysis of a liquid sample in a pipe whose temperature is approximately 70° C. for example and which, under the effect of a temperature drop, separates into two phases (phenomenon known as demixing). The proceeds analyzes for example according to the steps described above in Example 1, the sample then being injected into a differential refractometer for analysis.

What is claimed is:

1. A process for analyzing a fluid sample comprising:
   collecting a fluid sample in a sampling unit having a cavity for containing the fluid, at least one passage which connects the cavity to a source of the fluid sample to aspirate the fluid sample from the fluid sample source into the cavity and from which the fluid sample is injected into an analyzer device, a pressure varying device disposed in the cavity which provides control of pressure of the fluid sample in the cavity and a heat source which heats the fluid sample in the cavity;
   controlling at least one of the pressure of the fluid sample in the cavity with the pressure varying device and the temperature of the fluid sample in the cavity with the heat source to maintain the sample in the cavity to have at least one of pressure and temperature substantially identical to at least one of the pressure and the temperature of the sample at a time of collection in the cavity from the fluid source; and
   injecting the fluid sample from cavity into the analyzer device with at least one of the temperature and the pressure substantially identical to at least one of the temperature and pressure of the fluid sample in the cavity at the time of collection and thereafter analyzing the fluid sample.

2. A process in accordance with claim 1, wherein:
   the control of at least one of the pressure and the temperature maintains the sample in the cavity in a state of chemical equilibrium.

3. A process in accordance with claim 1, wherein:
   the control of at least one of the pressure and the temperature maintains the sample in the cavity in a state of thermodynamic equilibrium.

4. A process in accordance with claim 1, wherein:
   the control of at least one of the pressure and the temperature maintains the sample in the cavity in a state of chemical and thermodynamic equilibrium.

5. A process in accordance with claim 1, wherein:
   the heat source controls the temperature of the sample in the cavity between 20° C. and 200° C.

6. A process in accordance with claim 5, wherein:
   the heat source controls the temperature of the sample in the cavity between 20° C. and 150° C.

7. A process in accordance with claim 1, wherein:
   the pressure varying device maintains the pressure of the sample in the cavity between atmospheric pressure and 5 mPa.

8. A process in accordance with claim 1, wherein:
   the pressure varying device maintains the pressure of the sample in the cavity between atmospheric pressure and 3 mPa.

9. A process in accordance with claim 2, wherein the pressure varying device maintains the pressure of the sample in the cavity between atmospheric pressure and 5 mPa.

10. A process in accordance with claim wherein:
    the pressure varying device maintains the pressure of the sample in the cavity between atmospheric pressure and 3 mPa.

11. A process in accordance with claim 3, wherein:
    the pressure varying device maintains the pressure of the sample in the cavity between atmospheric pressure and 5 mPa.

12. A process in accordance with claim 3, wherein:
    the pressure varying device maintains the pressure of the sample in the cavity between atmospheric pressure and 3 mpa.

13. A process in accordance with claim 4, wherein:
    the pressure varying device maintains the pressure of the sample in the cavity between atmospheric pressure and 5 mpa.

14. A process in accordance with claim 4, wherein:
    the pressure varying device maintains the pressure of the sample in the cavity between atmospheric pressure and 3 mPa.

15. A process in accordance with claim 5, wherein:
    the pressure varying device maintains the pressure of the sample in the cavity between atmospheric pressure and 5 mPa.

16. A process in accordance with claim 5, wherein:
    the pressure varying device maintains the pressure of the sample in the cavity between atmospheric pressure and 3 mPa.

17. A process in accordance with claim 6, wherein:
    the pressure varying device maintains the pressure of the sample in the cavity between atmospheric pressure and 5 mPa.

18. A process in accordance with claim 6, wherein:
    the pressure varying device maintains the pressure of the sample in the cavity between atmospheric pressure and 3 mPa.

19. A process in accordance with claim 1, wherein:
    the fluid sample is obtained from a gas stream in a sulfur manufacturing amount.

20. A process in accordance with claim 1, wherein:
    the fluid sample is obtained from combustion fumes.

21. A process in accordance with claim 20, wherein the combustion fumes contain $SO_2$, $SO_3$, $N_2$, $O_2$, $H_2O$, $NO_x$, $H_2S$, $COS$, $CS_2$ and $NH_3$.

* * * * *